US00PP26286P2

(12) United States Plant Patent
Kordes

(10) Patent No.: US PP26,286 P2
(45) Date of Patent: Jan. 5, 2016

(54) FLORIBUNDA ROSE PLANT NAMED 'KORFLOCI46'

(50) Latin Name: *Rosa hybrida*
Varietal Denomination: KORfloci46

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 140 days.

(21) Appl. No.: 13/998,345

(22) Filed: Oct. 22, 2013

(51) Int. Cl.
*A01H 5/02* (2006.01)

(52) U.S. Cl.
USPC ..... Plt./151

(58) Field of Classification Search
USPC ..... Plt./151
See application file for complete search history.

*Primary Examiner* — Keith Robinson

(57) ABSTRACT

A new and distinct variety of rose with long lasting, novel red flowers, and attractive foliage with good disease resistance. It exhibits compact to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORfloci46'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2003. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORfloci46'.

SUMMARY OF THE INVENTION

The new rose plant may be distinguished from its seed parent, an un-named seedling, by the following combination of characteristics:

1. 'KORfloci46' has medium-sized flowers, whereas the un-named seedling has small flowers.
2. 'KORfloci46' has a very double petal count, whereas the un-named seedling has a semi-double petal count.

The new rose plant may be distinguished from its pollen parent, an un-named seedling, by the following combination of characteristics:

1. 'KORfloci46' has red flowers, whereas the un-named seedling has light red flowers.
2. 'KORfloci46' has a compact to bushy habit, whereas the un-named seedling has a bushy habit.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORfloci46' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORfloci46' was selected in May 2004 from the seedling beds to be asexually propagated for further evaluation. The first asexual propagation of 'KORfloci46' was done by budding in July 2004 at the inventor's nursery in Offenseth-Sparrieshoop, Germany.

These initial and other subsequent propagations conducted in controlled environments demonstrate that 'KORfloci46' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORfloci46' taken from plants of plants of 1 year of age.

DETAILED BOTANICAL DESCRIPTION

The following is a description of 'KORfloci46', as observed growing in September 2013 in a nursery in Jackson County, Oreg. on plants of 1 year of age. Color references are made using The Royal Horticultural Society (London, England) Colour Chart, 2001 except where common terms of color are used.

For a comparison, several physical characteristics of the rose variety 'KORfloci54', a rose variety from the same inventor described and illustrated in U.S. Plant patent application Ser. No. 13/987,162 and filed on Jul. 3, 2013 are compared to 'KORfloci46' in Chart 1.

CHART 1

| Characteristic | 'KORfloci46' | 'KORfloci54' |
|---|---|---|
| Flower size | Medium | Large |
| Flower color | Red | Salmon orange |
| Number of leaflets per leaf | 5 | 7 |

Parents:

*Seed parent*.—An un-named seedling.

*Pollen parent*.—An un-named seedling.

Classification:

*Botanical classification*.—*Rosa hybrida* 'KORfloci46'.

*Commercial classification*.—Floribunda rose.

FLOWER AND FLOWER BUD

Blooming habit: Continuous.

Flower bud:

*Size*.—Upon opening, 20 mm in length from base of receptacle to distal end of bud and 13 mm diameter at its widest point.

*Bud form*.—Short. Pointed ovoid.

*Bud color*.—As sepals first unfold, bud color is Red Group 46A. When ¼ open, the upper surface of petals is Red Group 43A, and the lower surface is Red Group 53C.

*Sepals*.—Color: Upper surface Yellow-Green Group 144B. Lower surface Yellow-Green Group 144A. Intonations of Greyed-Purple Group 183A. Size: Average 15-18 mm (l)×8 mm (w). Shape: Moderate foliaceous appendages on 3 of the five sepals. Apex: Apiculate. Base: Flat at union with receptacle. Quantity: Five. Surface texture: Upper side: Very pubescent. Lower surface: Lacking fine hairs. Stipitate glands: Abundant numbers along margins and on lower surface.

Flower bloom:

*Fragrance*.—None.

*Duration*.—On the plant 6-7 days. Senesced petals drop away cleanly.

*Size*.—Medium for a floribunda rose. When open, the average flower diameter is 50 mm and the average flower height is 20 mm.

*Form*.—Shape of flower when viewed from the side: Upon opening, upper part: Cupped. Upon opening, lower part: Concave. Open flower, upper part: Flattened convex. Open flower, lower part: Concave.

Color:

*Upon opening, petals*.—Outermost petals: Outer Side: Red Group 53C. Inner Side: Red Group 43A. Innermost petals: Outer Side: Red Group 46A. Inner Side: Red Group 46B.

*Upon opening, basal petal spots*.—Basal petal spot, outermost petals: Outer Side: Green-White Group 157D. Inner Side: Green-Yellow Group 1A. Basal petal spot, innermost petals: Outer Side: Green-White Group 157D. Inner Side: Green-Yellow Group 1A. Average Size: 1.5 mm (l)×2 mm (w).

*After opening, petals*.—Outermost petals: Outer Side: Red Group 53C with occasional stripe White Group 155C. Inner Side: Red Group 50A with occasional stripe White Group 155C. Innermost petals: Outer Side: Red Group 53D with occasional stripe White Group 155C. Inner Side: Red Group 50A with occasional stripe White Group 155C.

*After opening, basal petal spots*.—Basal petal spot, outermost petals: Outer Side: White Group 155C. Inner Side: White Group I55C. Basal petal spot, innermost petals: Outer Side: No distinctive coloration at petal base observed. Inner Side: No distinctive coloration at petal base observed. Average Size: 1.5 mm (l)×2 mm (w).

General tonality: On open flower Red Group 45B. No change in the general tonality at the end of the 7$^{th}$ day. Afterwards, general tonality is Red Group 46A to Red Group 46B.

Petals:

*Flower type*.—Very Double.

*Average range petal count*.—Approximately 110-120 petals under normal conditions.

*Petal reflex*.—Petals reflex slightly.

*Petal margin*.—Entire.

*Petal shape*.—Obovate. Apex: Obtuse. Base: Cuneate.

*Petal size*.—18-22 mm (l)×12-25 mm (w).

*Thickness*.—Average.

*Petal arrangement*.—Not formal.

*Texture*.—Inner Surface: Smooth. Outer Surface: Smooth.

Petaloids:

*Petaloid count*.—Average of 10-12 per flower.

*Petaloid size*.—7-10 mm (l)×3-7 mm (w).

*Petaloid color*.—Inner side: Red Group 46A. Outer side: Red Group 46B.

*Petaloid texture*.—Outer Side: Smooth. Inner Side: Smooth.

*Margins*.—Entire.

*Petaloid shape*.—Most commonly spatulate with some petaloids highly irregular. Apex: Obtuse. Base: Attenuate.

Reproductive organs:

*Pistils*.—Average. Approximately 25 present. Stigmas: Location: Equivalent in position to anthers. Color: Greyed-Yellow Group 160B. Styles: Length: About 8 mm long. Color: Green-White Group 157D with intonations of Red-Purple Group 61B.

*Stamens*.—Approximately 25 on average and regularly arranged. Anthers: Size: Average 2 mm (l)×1.5 mm (w). Pollen: Generally present. Color: Greyed-Orange Group 163B. Filaments: Color: Green-Yellow Group 1A with intonations of Red-Purple Group 61 B. Length: 6-7 mm.

*Receptacle*.—Surface: Lightly pubescent. Color: Yellow-Green Group 144A with intonations of Greyed- Purple Group 187B. Shape: Urn-shaped. Texture: Smooth. Size: 7 mm (h)×8 mm (w).

*Pedicel*.—Surface: With fine hairs and stipitate glands. Length: 30-35 mm average length. Diameter: 2 mm average diameter. Color: Yellow-Green Group 144A with intonations of Greyed-Purple Group 187C. Strength: Somewhat strong. Texture: Smooth.

*Peduncle*.—Length: 35-45 mm average length. Diameter: 2.5-3 mm average diameter. Color: Yellow-Green Group 144A with intonations of Greyed-Purple Group 187C. Strength: Strong. Borne: Multiple flower buds per stem, generally 2 to 5. Flowers held upright.

THE PLANT

Growth: Vigorous growth.

Plant habit: Compact to bushy. When grown as a field plant, the average plant height is 85 cm and the average plant width is 85 cm.

Stems:

*Stem color*.—Young wood: Yellow-Green Group 144A. Older wood: Yellow-Green Group 144A.

*Intonations*.—Greyed-Purple Group 183A.

*Stem surface texture*.—Young wood: Smooth. Older wood: Rough.

Prickles: Present.

*Incidence*.—Average of 15 per each 10 cm of stem.

*Size*.—Average length: 7 mm.

*Color*.—Immature prickles: Greyed-Purple Group 183A. Mature prickles: Greyed-Yellow Group 160A. Senescing to Greyed-Orange Group 177C.

*Shape*.—Concave.

*Texture*.—Smooth.

Leaves: Normally 5 leaflets on normal leaves in middle of the stem.

*Venation pattern*.—Pyramidal net pattern.

*Leaf size*.—110 mm (l)×75 mm (w).

*Abundance*.—Very.

*Surface*.—Upper side of leaf: Semi-glossy. Under side of leaf: Matte.

*Texture*.—Upper side of leaf: Smooth. Under side of leaf: Smooth.

Leaflets:

*Size*.—Average size of the terminal leaflet is 45 mm (l)×32 mm (w).

*Shape*.—Elliptic. Base: Obtuse. Apex: Acute.

*Margins*.—Finely serrated.

*Surface*.—Upper side of leaflet: Semi-glossy. Under side of leaflet: Matte.

*Texture*.—Upper side of leaflet: Smooth. Under side of leaflet: Smooth.

*Color, mature foliage*.—Upper Leaflet Surface: Green Group 137A. Lower Leaflet Surface: Green Group 137D.

*Color, juvenile foliage*.—Upper Leaflet Surface: Green Group 138A. Lower Leaflet Surface: Green Group 138B.

*Anthocyanin intonation*.—Greyed-Purple Group 183A. Location: Upper and lower surfaces of leaflet.

*Arrangement*.—Odd pinnate.

*Venation*.—Reticulate.

Stipules:

*Size*.—18 mm (l)×5 mm (w).

*Stipule color*.—Green Group 137B.

*Anthocyanin*.—Greyed-Purple Group 187C.

*Stipitate glands*.—Abundant numbers along margins.

*Texture*.—Smooth.

*Shape*.—Apex: Aristate. Base: Flat.

Petiole:

*Length*.—Average 25 min.

*Diameter*.—Average 2 mm.

*Petiole color*.—Yellow-Green Group 146B. Underneath: Yellow-Green Group 146C.

*Anthocyanin*.—Greyed-Purple Group 183A.

*Prickles*.—A few small prickles underneath.

*Stipitate glands*.—Limited numbers along margins.

*Texture*.—Smooth.

Petiole rachis:

*Length*.—Average 20 mm.

*Diameter*.—Average 1 mm.

*Color*.—Yellow-Green Group 146B. Anthocyanin present on juvenile tissue: Greyed-Purple Group 183A.

*Prickles*.—A few small prickles underneath.

*Stipitate glands*.—Limited numbers along margins.

Hips/seed formation: None observed.

Winter hardiness: To date, the variety has been grown successfully in Zone 6.

Disease resistance: Good resistance to Powdery mildew (*Sphaerotheca pannosa*) and blackspot (*Diplocarpon rosae*) diseases under normal growing conditions in Jackson County, Oreg.

I claim:

1. A new and distinct variety of rose plant, as described and illustrated herein.

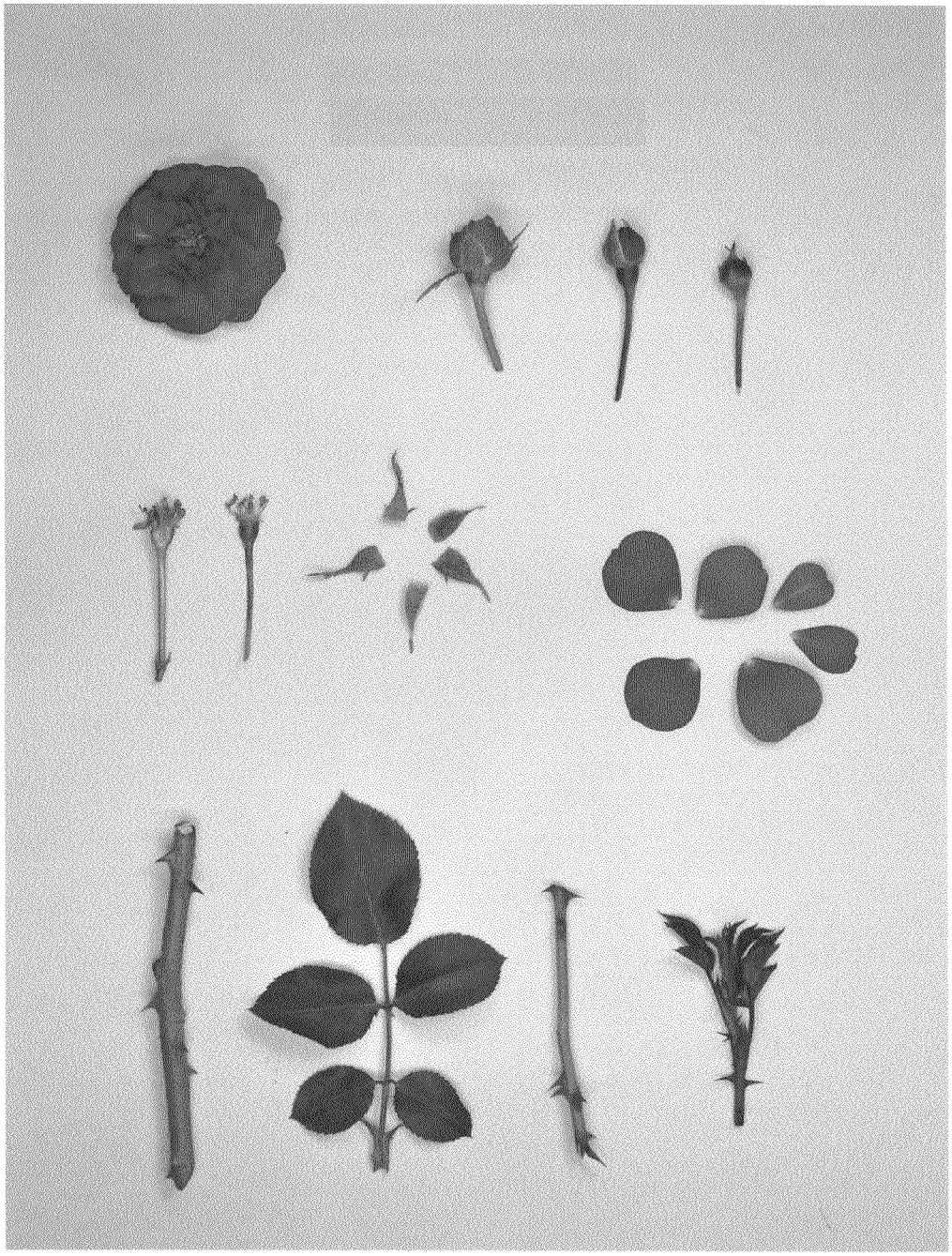

* * * * *